(12) United States Patent
Barthold

(10) Patent No.: US 8,470,015 B2
(45) Date of Patent: Jun. 25, 2013

(54) INSERTION SYSTEM FOR DEPLOYMENT OF CATHETER-BASED STENT DEVICES

(75) Inventor: Franz-Peter Barthold, Balingen (DE)

(73) Assignee: JOTEC GmbH, Hechingen (DE)

( * ) Notice: Subject to any disclaimer, the term of this patent is extended or adjusted under 35 U.S.C. 154(b) by 809 days.

(21) Appl. No.: 12/560,302

(22) Filed: Sep. 15, 2009

(65) Prior Publication Data
US 2010/0070017 A1   Mar. 18, 2010

(30) Foreign Application Priority Data
Sep. 16, 2008  (DE) .......................... 10 2008 048 533

(51) Int. Cl.
*A61F 2/06* (2006.01)
(52) U.S. Cl.
USPC ........................................ 623/1.11; 623/1.12
(58) Field of Classification Search
USPC ...................... 623/1.11, 1.12, 1.34, 2.11, 900
See application file for complete search history.

(56) References Cited

U.S. PATENT DOCUMENTS

| | | | |
|---|---|---|---|
| 3,628,535 A * | 12/1971 | Ostrowsky et al. | ............ 606/205 |
| 4,411,653 A | 10/1983 | Razi | |
| 5,026,377 A | 6/1991 | Burton et al. | |
| 5,707,376 A | 1/1998 | Kavteladze et al. | |
| 5,725,549 A * | 3/1998 | Lam | .............................. 623/1.34 |
| 5,944,727 A | 8/1999 | Ahari et al. | |
| 6,136,006 A | 10/2000 | Johnson et al. | |
| 6,514,261 B1 | 2/2003 | Randall et al. | |
| 7,105,016 B2 | 9/2006 | Shiu et al. | |
| 2003/0028235 A1 * | 2/2003 | McIntosh et al. | ............ 623/1.11 |
| 2003/0191516 A1 | 10/2003 | Weldon et al. | |
| 2004/0138734 A1 | 7/2004 | Chobotov | |
| 2004/0176682 A1 | 9/2004 | Murphy | |
| 2006/0184238 A1 | 8/2006 | Kaufmann et al. | |

FOREIGN PATENT DOCUMENTS

| | | |
|---|---|---|
| DE | 69806 550 | 11/2002 |
| DE | 10335 649 | 2/2005 |
| DE | 102004023559 | 9/2005 |
| DE | 10 2005 059 261 | 6/2007 |
| EP | 1 210 959 | 6/2002 |
| EP | 1 391 181 | 2/2004 |
| EP | 1 415 616 | 5/2004 |
| EP | 1 440 671 | 7/2004 |

(Continued)

OTHER PUBLICATIONS

European Search Report for European Patent Application No. EP09169903 dated Dec. 23, 2009.

*Primary Examiner* — Brian E. Pellegrino
(74) *Attorney, Agent, or Firm* — Knobbe Martens Olson & Bear, LLP

(57) ABSTRACT

An insertion system for release of a self-expanding stent device 18 in a body vessel has a first grip 33, which is fixedly connected to a shaft 15, a second grip 36, which is mounted on the shaft 15 to be movable in axial direction, a sheath 19, which, in a distal portion thereof, keeps the stent device radially compressed and which is fixedly connected to the second grip 36, and a retention element 17, which is fixedly connected to the shaft 15 and is guided in the sheath 19, wherein the retention element 17 holds the stent device 18 in its axial position relative to the first grip 33 when the sheath 19 is being retracted. Reference means 25 with an optical reference mark 26 are arranged for continuous monitoring of the axial position of the stent device 18.

13 Claims, 12 Drawing Sheets

FOREIGN PATENT DOCUMENTS

| | | |
|---|---|---|
| EP | 1 440 672 | 7/2004 |
| EP | 1 117 341 | 12/2004 |
| EP | 1 894 545 | 3/2008 |
| EP | 1 923 024 | 5/2008 |
| EP | 1 943 988 | 7/2008 |
| WO | WO 00/18330 | 4/2000 |

\* cited by examiner

INSERTION SYSTEM FOR DEPLOYMENT OF CATHETER-BASED STENT DEVICES

CROSS-REFERENCE TO RELATED APPLICATION

This application claims priority from German patent application DE 10 2008 048 533.0 filed on Sep. 16, 2008. The content of the above patent application is incorporated by reference herein in its entirety.

BACKGROUND OF THE INVENTION

1. Technical Field

The present invention relates to an insertion system for release of a self-expanding stent device in a body vessel, comprising a first grip, which is fixedly connected to a shaft, a second grip, which is mounted on the shaft to be movable in axial direction, a sheath, which, in a distal portion thereof, keeps the stent device radially compressed and which is fixedly connected to the second grip, and a retention element, which is fixedly connected to the shaft and is guided in the sheath, wherein the retention element holds the stent device in its axial position relative to the first grip when the sheath is being retracted.

2. Background Art

Insertion systems and stent devices of this kind are known, for example, from U.S. Pat. No. 5,026,377 A.

With such insertion systems, stent devices are implanted into blood vessels for the treatment of damages in blood vessels like, for example, aneurysms. Such treatment is applied, for example, in the surgical reconstruction of major blood vessels, for example the descending part of the thoragic aorta, that cannot be treated by conventional surgical methods because of insufficient accessibility. Examples of indications which are to be treated in this way, and as a result of which the function of the vessels is greatly impaired or there is a danger of rupture of the vessels, include blood vessel damage caused by disease or the like, acquired or congenital aneurysms or partial occlusions of the lumen of a blood vessel, for example by formation of pseudolumina.

Various implantable stent devices are known by means of which blood vessels, for example arteries, are kept open or widenings are excluded from the blood stream. These include stents and stent grafts.

Stents generally comprise a tubular body which is inserted into the vessel and is expanded and fixed at the appropriate site in order to keep open the lumen of the vessel.

Stent grafts comprise, for example, a series of stents or, respectively, a wire framework made of a self-expanding material. In this context, stents are understood to be individual self-expanding elements. The self-expanding elements or, respectively, the wire framework are connected to each other by a textile or PTFE tube, called a graft sleeve, to form a functional unit and in this way, analogous to the stents described above, they form a tubular body that supports the vessel walls.

Further, stent devices are known which, in addition to a stent graft, also comprise a woven prosthesis part, a so-called prosthesis cuff, attached to the proximal end of the stent graft.

Here, and also in the text below, "proximal" designates as usual a side directed towards the user (operator), and "distal" designates a side directed away from the user.

Such a prosthesis cuff enables a secure surgical fixation of the stent device to the vessel wall and, by virtue of its relative flexibility, can be used as a vessel adapter for connecting an implanted stent graft to other vessel reconstruction implants or to a vessel itself, for example in vascular reconstruction of the aortic arch.

In the principle described in U.S. Pat. No. 5,026,377 A mentioned at the outset, the insertion system has a first grip, which is fixedly connected to a proximal end of a shaft. Further, a second grip, which is fixedly connected to a sheath, is arranged movably on the shaft. Here, "fixedly" means that the connection between second grip and sheath is suitable for taking up tension, compression and torsion forces. Arranged between sheath and shaft there is a stent device, which is disposed inside the sheath and is radially compressed by the latter. The cross-section of the stent device is in this way greatly reduced, and it can be easily inserted into a vessel. When the sheath is then retracted relative to the stent device by a movement of the second grip, the stent device, by virtue of the resiliency of the metal frame or metal stent, expands back to its original shape in the portion of the stent device released from the sheath. The sleeve surface of the stent device is thereby stretched out and wedges itself within the blood vessel.

For implantation, the stent devices are first inserted into the blood vessel with the aid of catheters, which are advanced through the vessel lumen, and they are positioned at the correct location in the vessel. In this context, "deployment position" is understood as the whole area of a vessel filled by a stent device after expansion thereof. The term "landing zone" is understood as a short proximal area of the deployment position at which the stent device is surgically connected to the vessel wall after expansion.

By contrast, the "deployment zone" designates the area of the insertion system at whose axial level, after expansion, the part of the stent device is located which is to be surgically connected to the vessel wall. In the case of an insertion system loaded with a non-foreshortening stent device, the deployment zone is accordingly situated at the axial level of a proximal portion of the stent device compressed in the sheath. In the case of an insertion system with a non-foreshortening stent device having a prosthesis cuff portion provided at its proximal end, the deployment zone can be offset in proximal direction, relative to the proximal end of the stent device compressed in the sheath, to such an extent that it corresponds to the position of the distal portion of the prosthesis cuff after the expansion and unfolding of the stent device, if the stent device is to be connected to the vessel wall at the distal end of the prosthesis cuff portion after the expansion and subsequent unfolding of the prosthesis cuff portion.

By contrast, in the case of an insertion system with a foreshortening stent device, the deployment zone can be offset in distal direction, relative to the proximal end of the stent device compressed in the sheath, to such an extent that it corresponds to the position of the proximal portion of the stent device in its unfolded state.

The correct position of the stent device can be monitored, for example, by X-ray markers. However, the continuous monitoring of the position by X-ray markers exposes the operator and patient to a certain amount of radiation. Particularly in operations performed on an openly accessible aortic stump, in which the landing zone for the stent is directly visible with the naked eye, for example in procedures on the thoracic part of the descending aorta, continuous monitoring of the position by X-ray markers is therefore not only an unnecessary risk but also extremely complicated, since there is no blood flow. This is because the patient is connected to a heart-lung machine during these operations such that the diseased vessel can be opened, because it is empty of blood.

In the context of transluminal treatment of blood vessels, a number of other techniques for positional control of a stent device or of another medical device are known, which techniques do not or only to a minor extent employ X-radiation.

For example EP 1 943 988 A1 describes an insertion system for a stent device, in which positional control of the stent device is achieved by sensors provided on the insertion system or the stent device. These sensors operate on the basis of non-ionizing radiation, magnetic fields or pressure waves.

EP 1 391 181 A1 describes an apparatus for virtual endoscopy, in which apparatus the position of a surgical instrument is determined by means of sensors provided on the surgical instrument, and the data acquired are transmitted to an imaging system for generating a virtual representation of the patient's body and the surgical instrument inserted therein.

DE 10 2005 059 261 A1 describes a catheter device for the treatment of a vessel obstruction, which catheter device has one or more sensor systems provided on its distal end, for image recording and three-dimensional gauging of the vessel to be treated.

These techniques and devices, however, have the disadvantage that they require expensive equipment, which as well is generally very sensitive to technical failure and sensing errors resulting, for example, from external cues. For instance, metallic objects in the vicinity of the operation field might disturb magnetic fields used for determining the position of the medical device.

Further, the technical complexity of the sensor systems results in high production costs, hence being especially disadvantageous in single-use surgical instruments such as insertion devices for stent devices.

After the stent device has been positioned in the vessel, according to the teaching of U.S. Pat. No. 5,026,377 A mentioned at the outset, the sheath is retracted in the proximal direction. In this process, the stent device lies in contact with a retention element, which holds the stent device in its axial position relative to the first grip while, with the aid of the second grip, the sheath also enclosing the retention element is pulled off from the stent device to permit expansion thereof.

When a self-expanding stent device is released in this way, the operator often has to exert a considerable force on the second grip, connected to the sheath, and on the first grip, connected to the shaft and to the retention element.

During this process, the large amount of force to be applied is mainly caused by friction between the outer wall of the stent device, strongly compressed against its expansion forces, and the inner wall of the sheath.

When pulling back the sheath, the operator, at the same time, has to take care not to shift the stent device axially away from the site at which it is intended to be specifically placed.

In this connection, various methods, stent devices and stent insertion systems are known, for example from EP 1 923 024 A2 or EP 1 440 672 A1, in which shifting of the stent is intended to be avoided by anchoring of the stent in the vessel wall in good time.

However, a disadvantage of this is that, for example with stent parts penetrating into the surrounding vessel wall, additional trauma may be caused. Moreover, the known methods and devices do not offer any certainty of a proximal portion of the stent device coming into contact with the vessel wall at its predetermined landing zone. Consequently, in the event of incorrect handling by the operator, the stent device may shift out of position, for example in distal direction, which in some circumstances is associated with the formation of folds, for example in a graft sleeve. Such folds pose an additional risk in the area of the inner wall of a stent device that has been inserted in this way. Secure anchoring of the proximal end in the vessel wall is also made more difficult, and the imprecision of the proximal deployment position may compromise the overall success of the operation.

During the course of the operation, this shifting of the stent device as a whole, or at its proximal end or distal end, can be avoided by not moving the stationary parts of the stent insertion system, especially the shaft and the first grip, relative to the deployment position, such that the deployment zone remains unchanged in position relative to the landing zone.

In the known stent insertion systems, the operator can ensure the unchanged position of the stent device relative to the body vessel, and, therefore, relative to the axial deployment position, only by precisely controlling the hold on the first grip of the stent insertion system. However, since he at the same time has to use his other hand on the second grip to carry out the withdrawal movement, there is a high probability of the withdrawal movement, or of compensatory movements in the opposite direction, causing the stent device to shift, at least partially, in axial direction relative to the predetermined landing zone. This shifting may compromise the success of the operation or even cause damage to the vessel wall.

DISCLOSURE OF THE INVENTION

In view of the above, it is an object of the present invention to improve the existing stent insertion systems in such a way that, while being of a simple construction, they make it easier to insert a stent device safely and in the correct position.

According to the invention, this and other objects are achieved by an insertion system of the kind mentioned at the outset, wherein reference means with an optical reference mark are provided for continuous monitoring of the axial position of the stent device.

The object underlying the invention is fully achieved in this way.

In this connection, the insertion system having reference means according to the invention is to be applied in surgical operations performed on locations inside the human body which during open surgery, are directly accessible and directly visible, i.e. without additional detection equipment, from outside the patient's body.

According to the invention, even after the expansion procedure has been started by pulling back the sheath, the reference mark now provides a visual aid with which the operator can monitor compliance with the predetermined deployment position of the stent device and can thus continuously monitor the axial position of the catheter and thereby the position of the deployment zone relative to the landing zone.

An optical reference mark is to be understood here as a mark which is designed such that it can be detected by the naked eye during an operation. This means that the operator, for detecting the optical reference mark, does not require additional equipment such as detection apparatuses and/or sensors as well as display means.

Moreover, in this context, a stent device is to be understood as a stent, a stent arrangement, a stent graft, or a stent graft with attached prosthesis cuff.

The inventors have thus not taken the approach of modifying existing methods for distal preliminary anchoring of a stent device, or, respectively, of making these methods less traumatic, but have instead found a way by which preliminary anchoring for maintaining the axial position is rendered entirely superfluous. Thus, the risks of injury inherent to preliminary anchoring and the technical risks posed by relatively complex equipment can be avoided and, in addition, problems, which cannot be solved by preliminary anchoring during insertion of stent systems, are in fact solved. This concerns in particular the previously discussed shifting of the proximal end of the stent device relative to its distal end.

It is also of advantage that the handling of existing stent insertion systems is improved in such a way that, when the sheath is retracted, continuous optical monitoring of the deployment zone by the operator is possible without the need for continuous use of X-rays or additional sensor or imaging equipment.

Errors on the part of the operator when deploying a stent device under visual monitoring conditions can thus be substantially avoided. The present invention also makes the first use by an operator much easier.

For example, in the device according to the invention, this is achieved by the reference means being designed such that they have a light source, for example a lamp or a light-emitting diode (LED) or a laser.

This light source can be integrated into the shaft or into the retention element, for example at the level of the deployment zone, such that the emitted light can be seen from outside through an at least partially translucent part of the shaft, of the stent device and/or of the sheath.

In such an arrangement, electrical leads routed upwards through the shaft can connect the light source to an external energy source, or to an energy source integrated into the first grip or mounted removably on the first grip, and to control elements.

Moreover, materials with light-conducting properties can be incorporated into the shaft, such that a light source, which is connected to an energy source and which is integrated for example into the first grip or mounted removably on the first grip, can be connected to the light-conducting materials in such a way that the emitted light is conveyed through the shaft until it strikes a refraction element at the level of the deployment zone, which element refracts the light such that it can be seen from outside through an at least partially translucent part of the shaft, of the stent device and/or of the sheath.

According to an object of the present invention, the reference means comprise a physical reference mark.

In the scope of the present invention, a "physical reference" mark is understood to be a reference mark that is formed from a body, which is placed near or at the vessel stump to be stented and which can there be seen with the naked eye, and, moreover, can be haptically detected inside the location to be treated without additional detection means required. Thus, the reference mark is arranged at the insertion system to be proximal to the stent device.

Hence, in situations where the area to be treated is covered with tissue or blood, the operator can continuously—or whenever this might be useful or necessary during an intervention—determine the position of the physical reference mark and thus monitor the axial position of the stent device during deployment thereof, just by touching or feeling the reference mark.

An advantage of this is that a physical reference mark is technically very insensitive, such that a failure during an operation can be largely ruled out.

Further, it is advantageous that the operator is at all times well able to see or at least feel a physical reference mark, for example even when viewing conditions are obstructed by blood.

In addition, it is possible to configure the physical reference mark by means of suitable choice of colour, for example blue or green, such that it provides a well visible colour contrast with the vessel to be treated and with its surrounding area. Moreover, by means of light sources, such as a lamp, LED and/or laser, it is possible to produce suitable internal lighting, for example routing electrical leads or light-conducting materials through the inside of the holding means from the physical reference mark to the grip, where they can be suitably connected, for example, to an energy source or light source removably provided on the grip.

According to a further object, the reference means comprise holding means which are connected to the physical reference mark and which, by way of a holding means head part, are connected to a stationary part of the insertion system. Here, it is particularly preferred if the holding means are rod-shaped or designed as a tube.

The advantage of the rod-shaped holding means is that the reference mark can in this way be easily uncoupled from the movement of the movable parts of the insertion system, in particular from the second grip and the sheath. Here, the holding means, which pass the second grip, are either routed outside the second grip or inside the second grip, the latter configuration possibly allowing easier operation.

If the holding means are designed as a tube, they are configured in a constructionally simple way; the tube is pushed over the catheter and can carry the physical reference means at the lower end or, respectively, can itself be designed as such physical reference means.

According to another object, the holding means have an axially defined length.

This ensures that the reference means are always located in a fixed axial position relative to the deployment zone.

According to a further object, the reference means are arranged thereon in such a way as to be at least partially removable.

This has the advantage that the reference means are exchangeable, and their use can thus be adapted to the conditions arising in each particular case, in particular to the vessel diameter.

It is also of advantage that the reference means can be removed when, during an operation, the necessity or desire arises for the operator to have direct access to the other components of the insertion system according to the invention or to the body vessel to be treated.

For this purpose, a holding means head part of the reference means can be provided with a fastening element which interacts in a suitably reversible manner with a suitable complementary fastening element, for example on the first grip. The temporary connection between the holding means head part and preferably the first grip can be established here, for example, by a plug-in connection or screw connection, or by other types of connections, for example adhesive connections, or combined forms of the aforementioned types of connections.

According to another object, the holding means head part comprises a recess.

It is advantageous here that, after release, the holding means head part can be removed laterally from the insertion system, without the need to further manipulate parts of the insertion system or to change the position of the insertion system.

Moreover, the physical reference mark may comprise a recess.

This has the advantage that, with suitable guidance of the holding means inside or outside the second grip, the reference means as a whole can be removed laterally from the insertion system without further manipulating parts of the insertion system or changing the position of the insertion system.

According to still a further object, the holding means head part is designed as a multi-piece part comprising a head part top segment and at least one head part bottom segment, wherein the head part top segment is movable relative to the head part bottom segment, said head part bottom segment bearing distally on said head part top segment, and wherein the head part top segment comprises means for securing the holding means head part on a stationary part of the insertion system.

Thus, for example, the head part bottom segment can be secured on the head part top segment such that it is reversibly removable or is mounted movably in at least one axis relative to the head part top segment. For example, the head part bottom segment can be connected to the head part top segment via a radially encircling holding element such that it is rotatable relative to the head part top segment and, therefore, relative to the first grip, wherein the rotation axis extends substantially parallel to the shaft. The head part bottom segment can also be connected to the head part top segment by a hinge, such that it can be removed, when necessary, from the distal portion of the stent insertion system, without releasing the reference means from the device.

These measures are therefore advantageous in terms of construction.

According to a further object, it is preferred if the physical reference mark is shaped substantially annular.

The advantage of this is that a reference mark with an annular shape is well visible from all sides. Further, an annular reference mark is well adapted to the substantially round cross section of a vessel, as a result of which a better marking of the deployment zone is achieved. In addition, by substantially avoiding sharp edges and corners, the risk of tissue damage is reduced.

The same advantages can also be achieved with the reference mark designed as a triangle, polygon, ellipse or other closed geometrical structure. These shapes too are regarded as "substantially annular" within the context of the present invention.

Further, the physical reference mark may according to one object comprise an external dimension smaller than the internal diameter of a body vessel to be treated.

This is particularly advantageous because it permits a very precise determination of the position of the deployment zone in relation to the landing zone, and the operator can thus more easily verify the desired axial orientation between deployment zone and landing zone.

According to another object, the physical reference mark comprises an internal dimension greater than the external diameter of the vessel wall of a body vessel to be treated.

This is particularly advantageous when operating on vessels having a small diameter relative to the diameter of the loaded insertion system, such that there is insufficient or barely sufficient space for insertion of the reference mark. This may be the case, for example, in the aorta of children. As the reference mark can be guided from outside over the stump of a body vessel, the insertion system can be inserted without causing tissue damage. Moreover, this greatly facilitates the determination of the relative axial position of the deployment zone to the landing zone.

According to a further object, the reference mark is arranged axially at substantially the same level as a deployment zone which represents that axial area of the insertion system, on the level whereof the area of the stent device to be brought into contact with the landing zone is located after expansion.

This has the advantage that the position of the deployment zone can be optimally determined in this way, that is to say preferably without any room for interpretation on the part of the operator.

According to still a further object, the reference mark is axially offset relative to the deployment zone.

In this case, the reference mark is preferably offset in the proximal direction relative to the deployment zone. In this connection, the axial distance between the deployment zone and the reference mark can be chosen such that, when the deployment zone is located at axially the same level as the landing zone, the reference mark lies at the same axial level as the upper rim of the vessel stump. Alternatively, the axial distance between the deployment zone and the reference mark can be chosen such that it is situated at a suitable distance, i.e. a distance easy to determine optically, from the upper rim of the vessel stump. A suitable distance between the distal end of the reference mark and the proximal rim or margin of the vessel stump can, for example, be between one millimetre and five centimetres.

The advantage of a reference mark offset in relation to the deployment zone lies, on the one hand, in better handling in narrow vessels and, on the other hand, in the better view the operator has of the edge of the sheath as soon as this approaches the upper end of the stent device compressed in the interior of the sheath. In this way, it is possible to avoid an uncontrolled and abrupt release of the stent device that can cause tissue damage.

Further advantages and features of the invention are set forth in the following description and in the attached figures.

It will be understood that the aforementioned features and the features still to be explained below can be used not only in the respectively specified combination but also in other combinations or on their own, without departing from the scope of the present invention.

BRIEF DESCRIPTION OF THE DRAWINGS

The aforementioned features of the invention and the features still to be explained below are shown in the figures, in which.

MODES OF CARRYING OUT THE INVENTION

Figure 1:
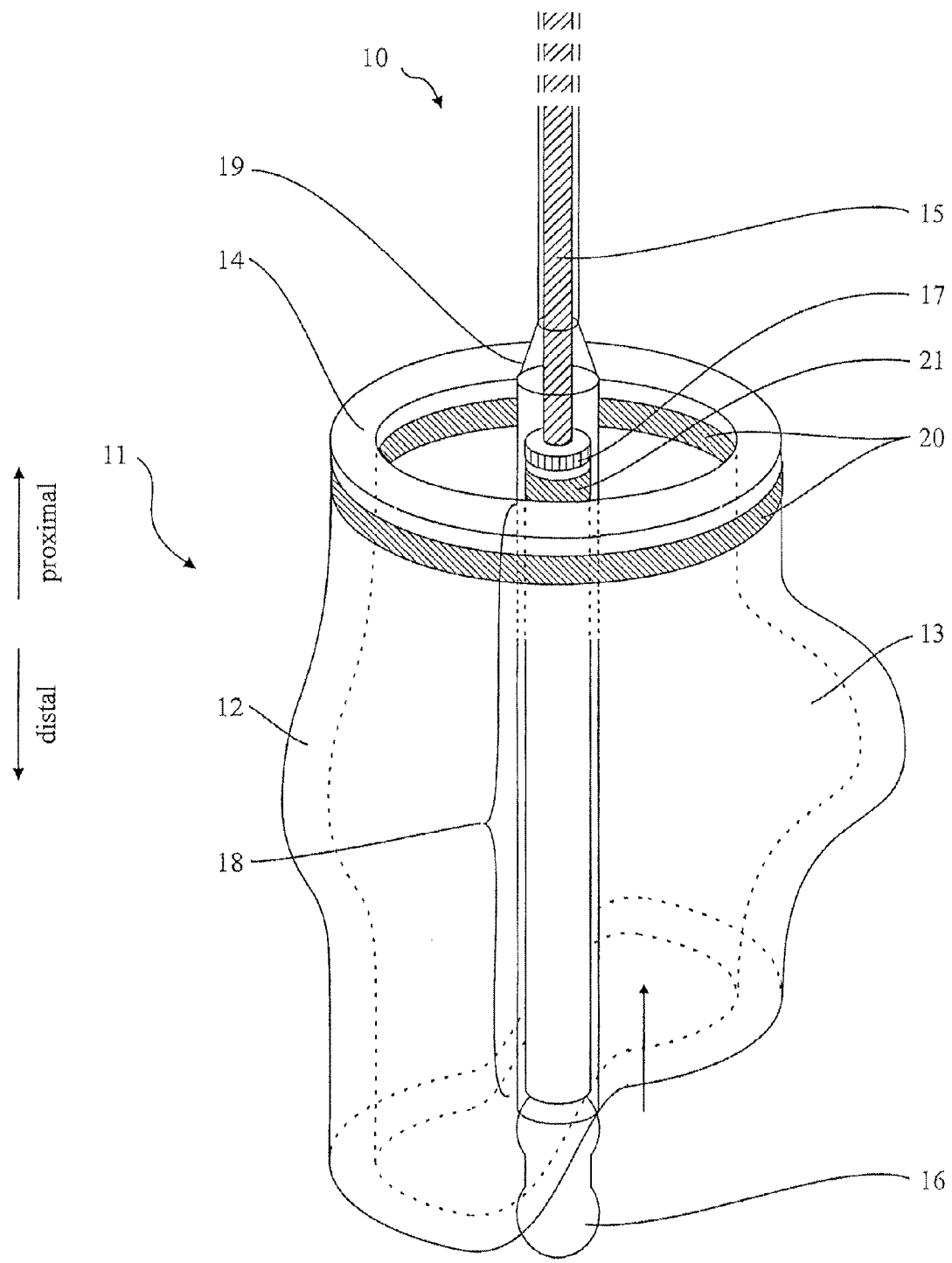
FIG. 1 shows a distal portion of a stent insertion system known from the prior art, which insertion system is inserted into the interior of a vessel stump.

FIG. 1 shows a known insertion system 10 introduced into a body vessel 11. The body vessel 11 has a vessel wall 12, an aneurysm 13 to be treated, and an upper margin or rim 14 at which the body vessel 11 is cut open. The insertion system 10 comprises a shaft 15, an atraumatic spherical tip 16, and a retention element 17. A stent device 18 is furthermore arranged in the insertion system 10 in such a way that it lies inside and is radially compressed by a distal portion of a sheath 19.

Further, a deployment zone 21 is indicated on insertion system 10, which deployment zone 21, during an operation, is ideally to be maintained directly opposite and at the same axial level as a landing zone 20 on the vessel wall 12 of body vessel 11.

Figure 2:
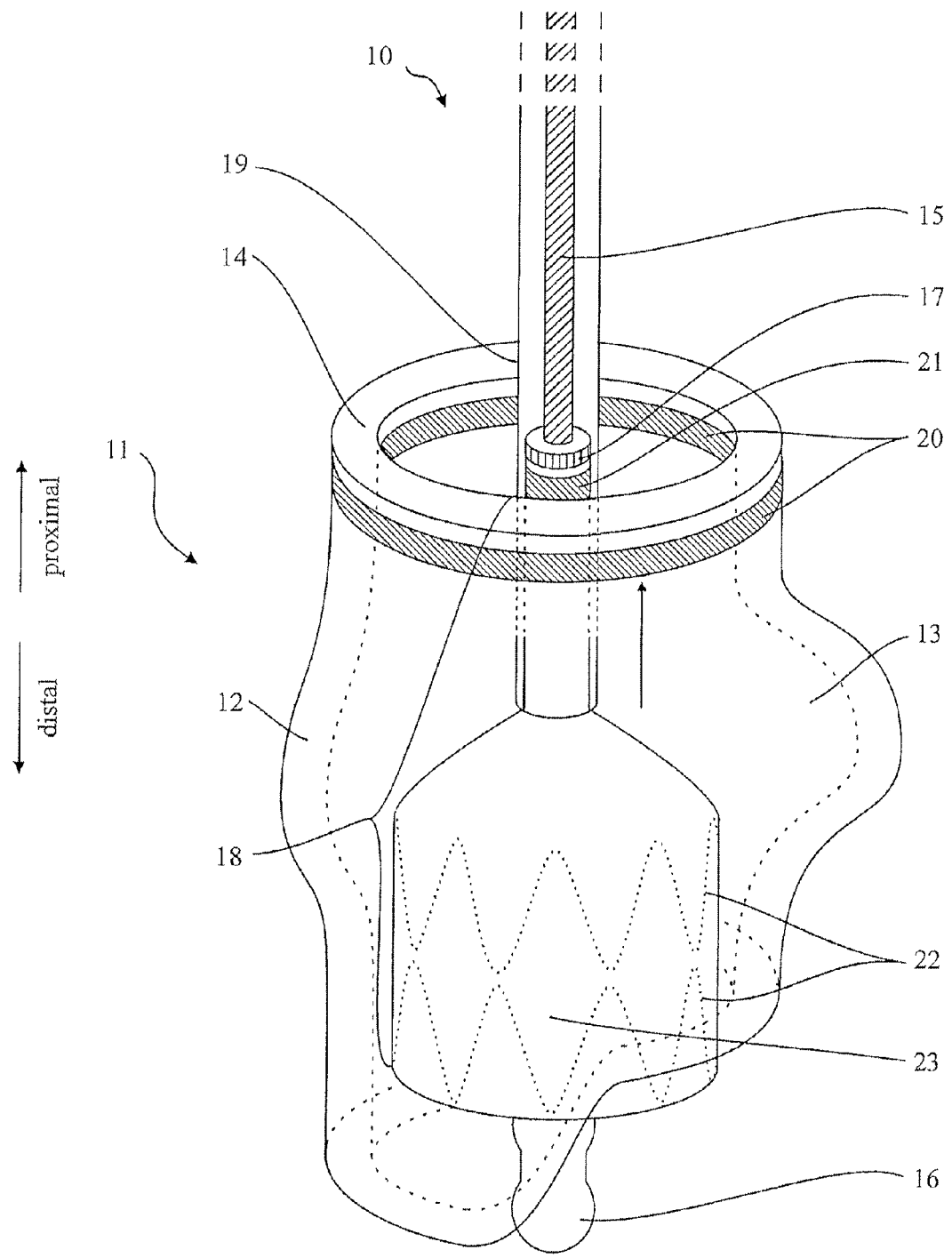
FIG. 2 shows the start of the deployment process of the stent device from the stent insertion system according to FIG. 1.

FIG. 2 shows the progress of a release procedure by means of the stent insertion system 10, where sheath 19 has been retracted proximally in axial direction compared to the view in FIG. 1, and stent device 18 has been partially released at its distal end. Here, on the released distal portion of stent device 18, stents 22 are shown which are functionally connected via a graft sleeve 23.

In this figure and in the following figures, only the parts that appear for the first time or that are important to the description are included with their reference signs in the respective figure description. Reference signs that are not mentioned are described in the descriptions of previous figures.

Figure 3:
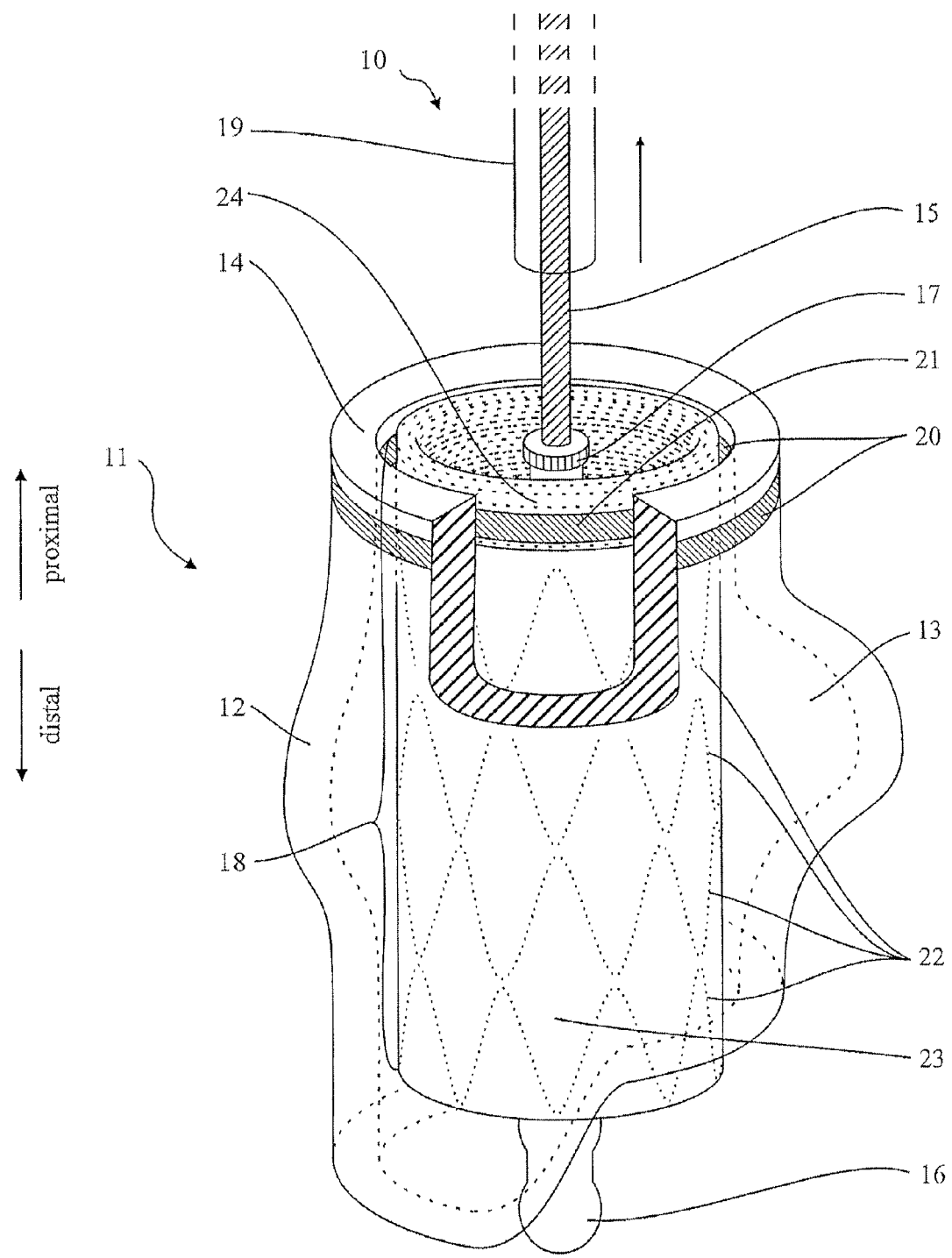
FIG. 3 shows the end of the deployment process of the stent device of FIG. 2.

FIG. 3 shows the end of the deployment process of the stent graft by means of the known stent insertion system. Here, sheath 19 has been further retracted in proximal axial direction compared to the views in FIGS. 1 and 2, and stent device 18 has been completely released. Moreover, a prosthesis cuff 24 previously stored in the interior of stent device 18 has been partially unfolded. It is of particular importance here that the deployment zone 21 at the distal end of the prosthesis cuff 24 comes into direct contact with the landing zone 20 at the proximal end of body vessel 11. The vessel wall 12 is shown partially cut away in the front area in order to better illustrate deployment zone 21.

Figure 4:
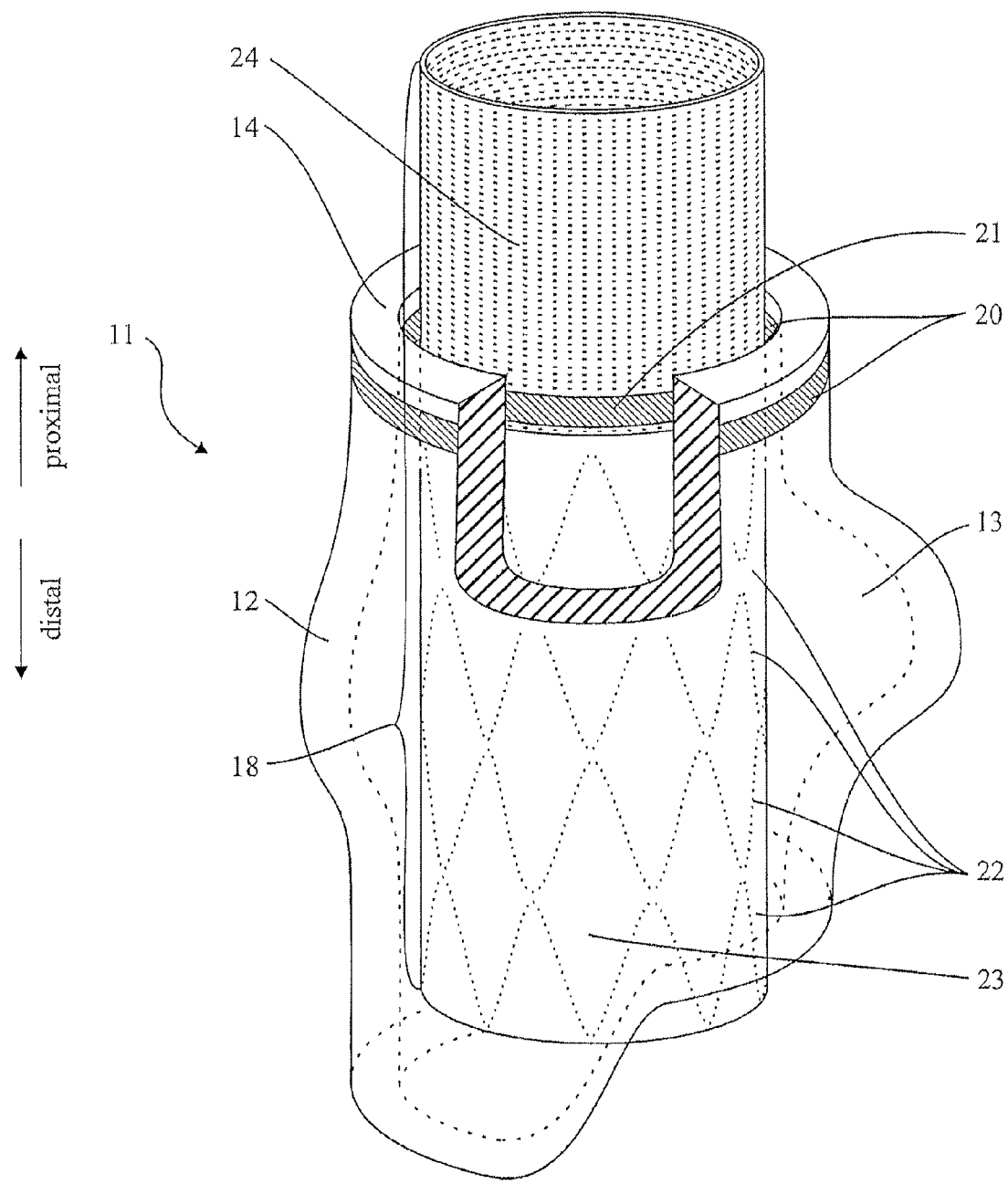
FIG. 4 shows the final state of the implanted stent device of FIG. 3, with the prosthesis cuff being spread out.

FIG. 4 shows the final stage of the process, stent device 18 being implanted into body vessel 11, with prosthesis cuff 24 now fully unfolded.

Figure 5:
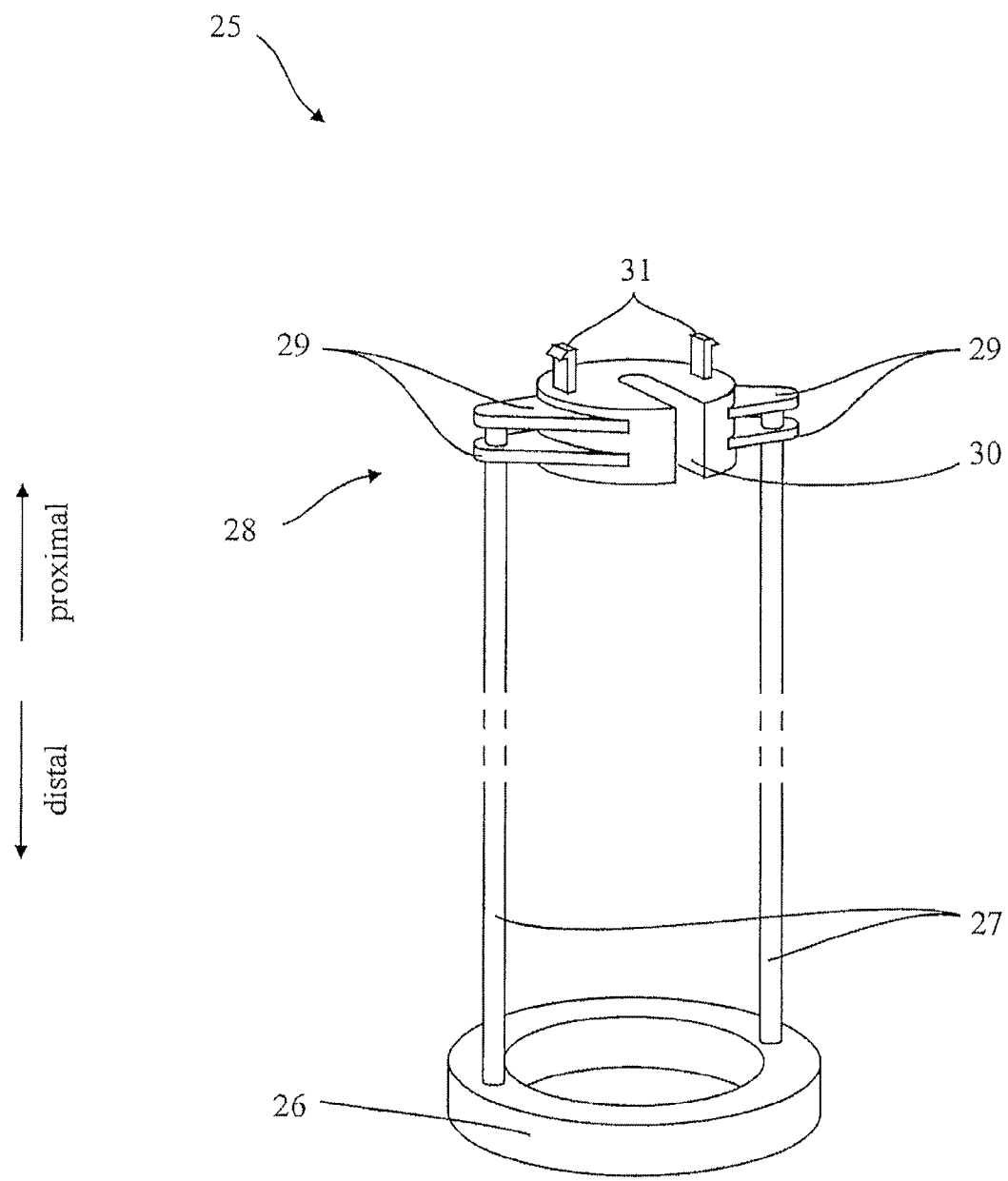
FIG. 5 shows an exemplary embodiment of the reference means according to the invention.

FIG. 5 shows reference means 25 according to the invention, which reference means 25 have a reference mark 26 in the form of a ring, and holding means 27 which are here formed by two rods. Holding means 27 connect reference mark 26 to a holding means head part 28. Holding means head part 28 comprises brackets 29 which act as spacers between holding means 27 and a second grip and through which the holding means 27 are guided and, respectively, are secured on holding means head part 28. Holding means head part 28 also has a recess 30 via which holding means head part 28 is placed onto shaft 15 of the insertion system. Further, holding means head part 28 also has locking means 31 provided at its proximal end, which locking means 31 interact with complementary locking means or recesses on a first grip in such a way that reference means 25 are mounted removably on the insertion system.

Figure 6:
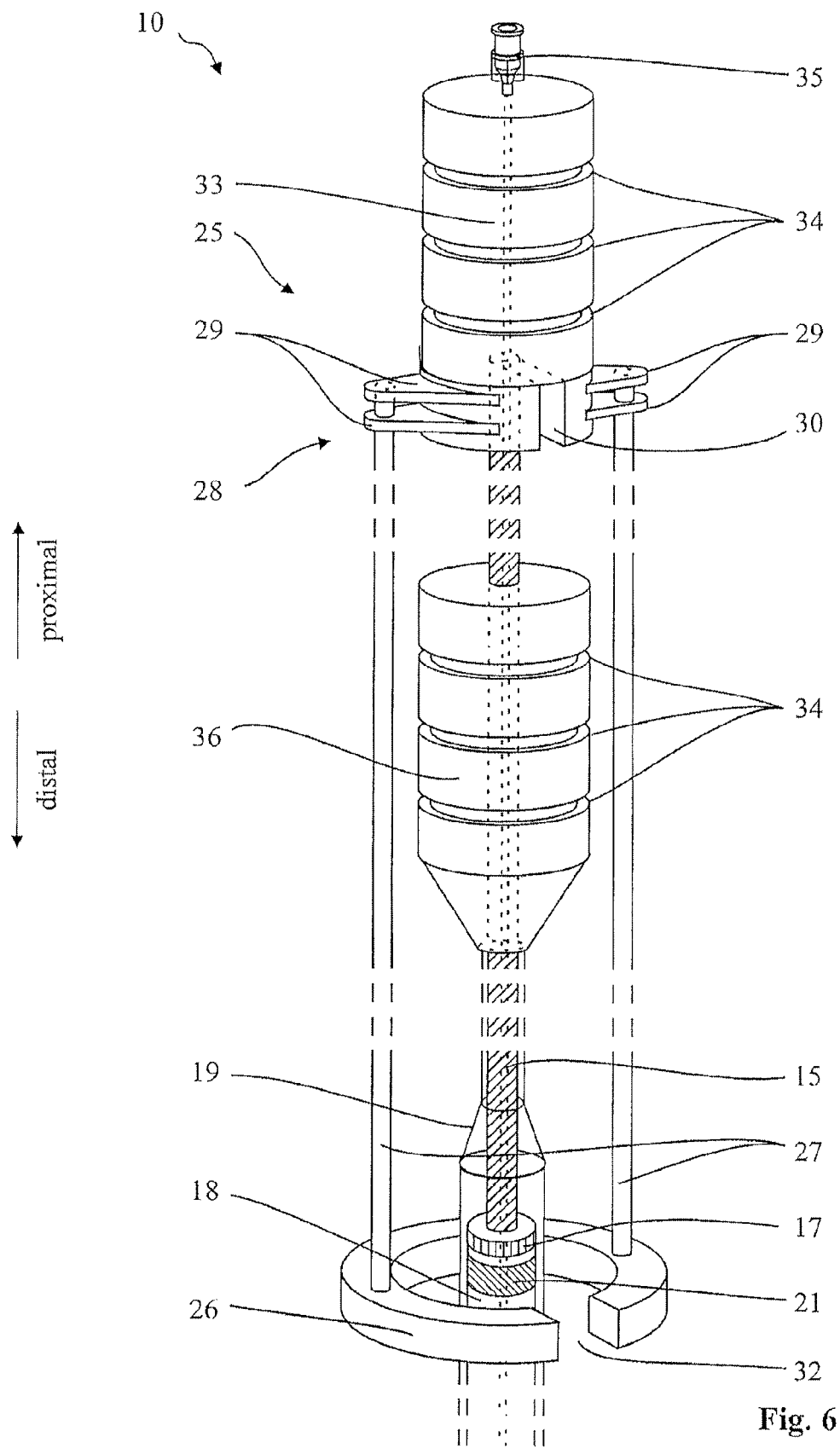
FIG. 6 shows an insertion system with the reference means of FIG. 5 guided outside the second grip.

FIG. 6 shows the insertion system 10 with a first grip 33 which has grip furrows 34 and is fixedly connected to shaft 15 and, at its upper end, has a passage 35 for a guide wire (not shown). Insertion system 10 is furthermore provided with a second grip 36 which has grip furrows 34, is fixedly connected to sheath 19, and is mounted movably in axial direction relative to shaft 15. Insertion system 10 furthermore comprises reference means 25 (shown in FIG. 5) in which annular reference mark 26 comprises a recess 32 and in which the holding means 27 are guided outside second grip 36.

Figures 7A, 7B:
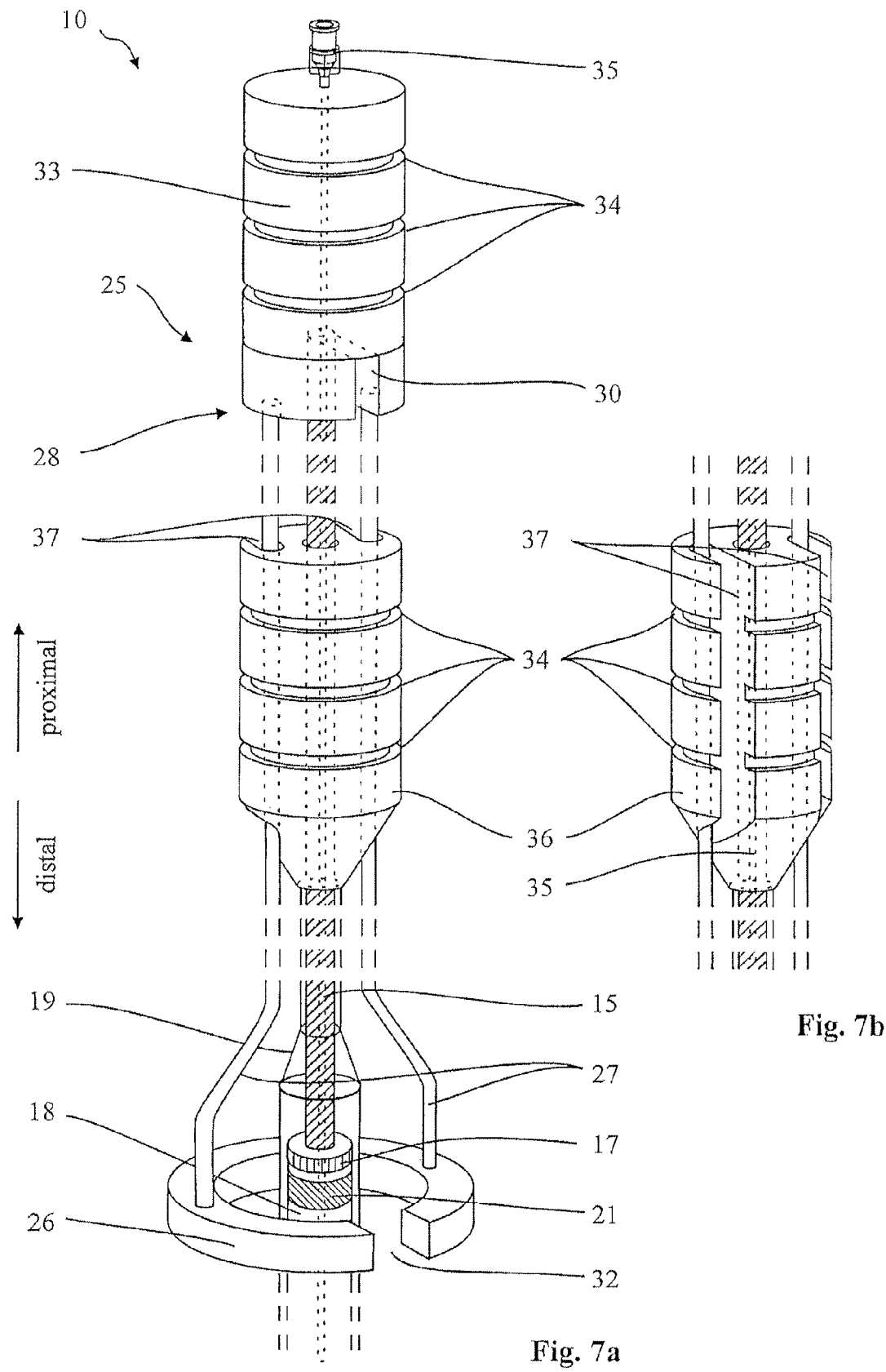
FIGS. 7a, 7b show an insertion system with the reference means of FIG. 5, here guided inside the second grip.

FIG. 7a shows insertion system 10 in which holding means 27 are guided through recesses 37 on second grip 36 in such a way that second grip 36 can be moved in axial direction relative to holding means 27. Recesses 37 on second grip 36 serve to release holding means 27 from second grip 36 during removal of reference means 25 from insertion system 10.

FIG. 7b shows a view of second grip 36 of the embodiment of FIG. 7a, with recesses 37 in which holding means 27 are received, this view being turned through 180° about the longitudinal axis in relation to FIG. 7a.

Figure 8A:
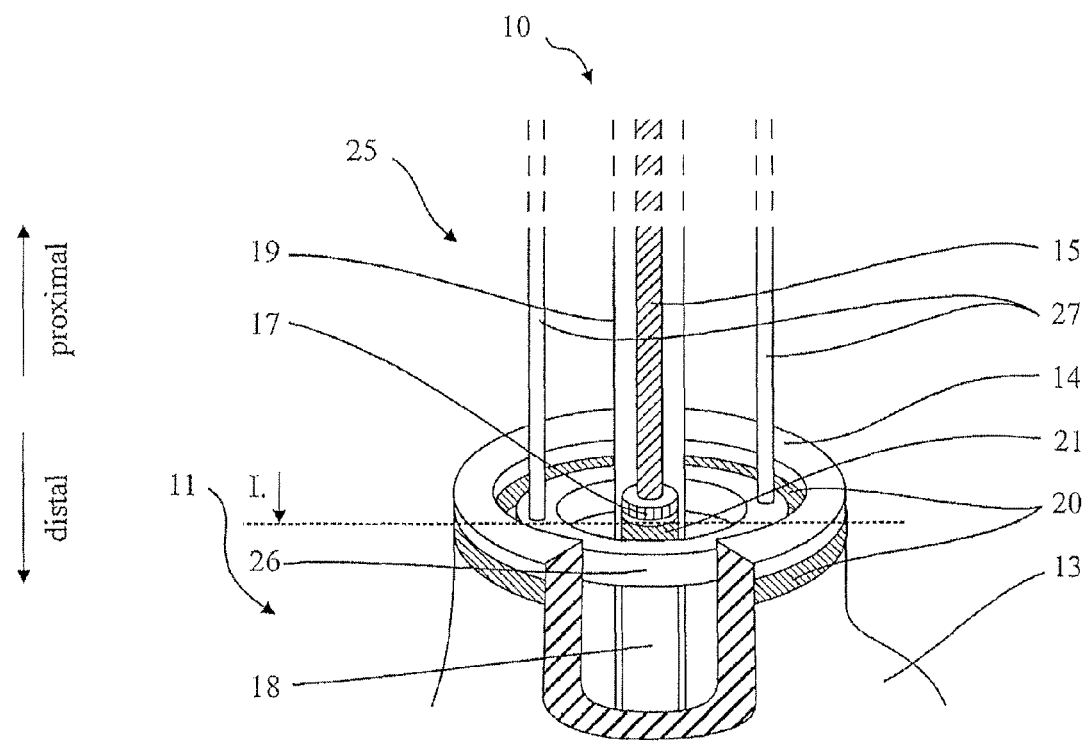
FIGS. 8a to 8f show various embodiments and positions of the physical reference mark.

FIG. 8a shows, in a view similar to FIG. 3, another embodiment of insertion system 10, in which annular reference mark 26 comprises an external diameter smaller than the internal diameter of body vessel 11 to be treated. Here, reference mark 26 is arranged at the same axial level as deployment zone 21 and is positioned opposite landing zone 20 in the proximal end of a body vessel 11.

Figure 8B:
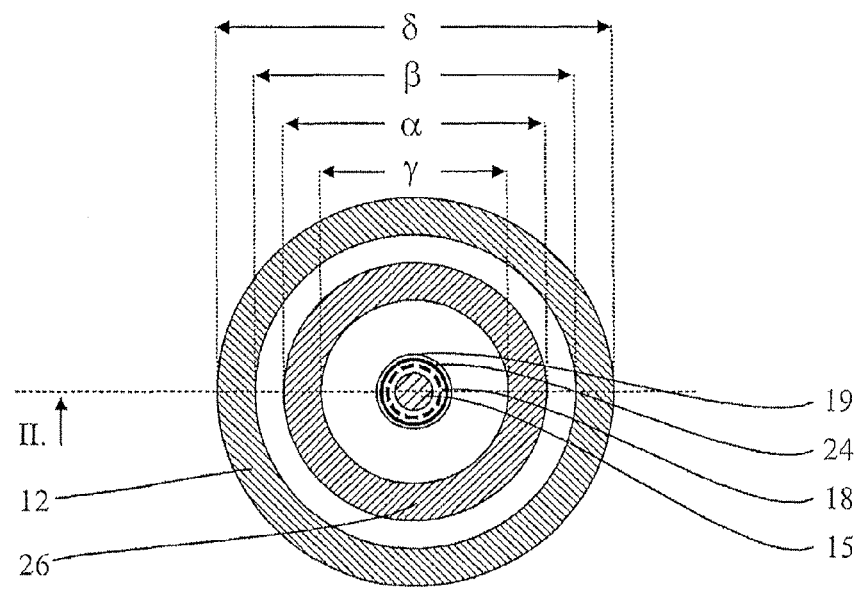

FIG. 8b shows a sectional view of insertion system 10 of FIG. 8a, at the level of the section line I from FIG. 8a. Here, reference mark 26, having an internal dimension $\gamma$ and an external dimension $\alpha$, is arranged inside of wall 12 of body vessel 11, having an internal diameter $\beta$ and an external diameter $\delta$. The internal diameter $\beta$ of vessel wall 12, here, is greater than the external dimension $\alpha$ of reference mark 26.

Figure 8C:
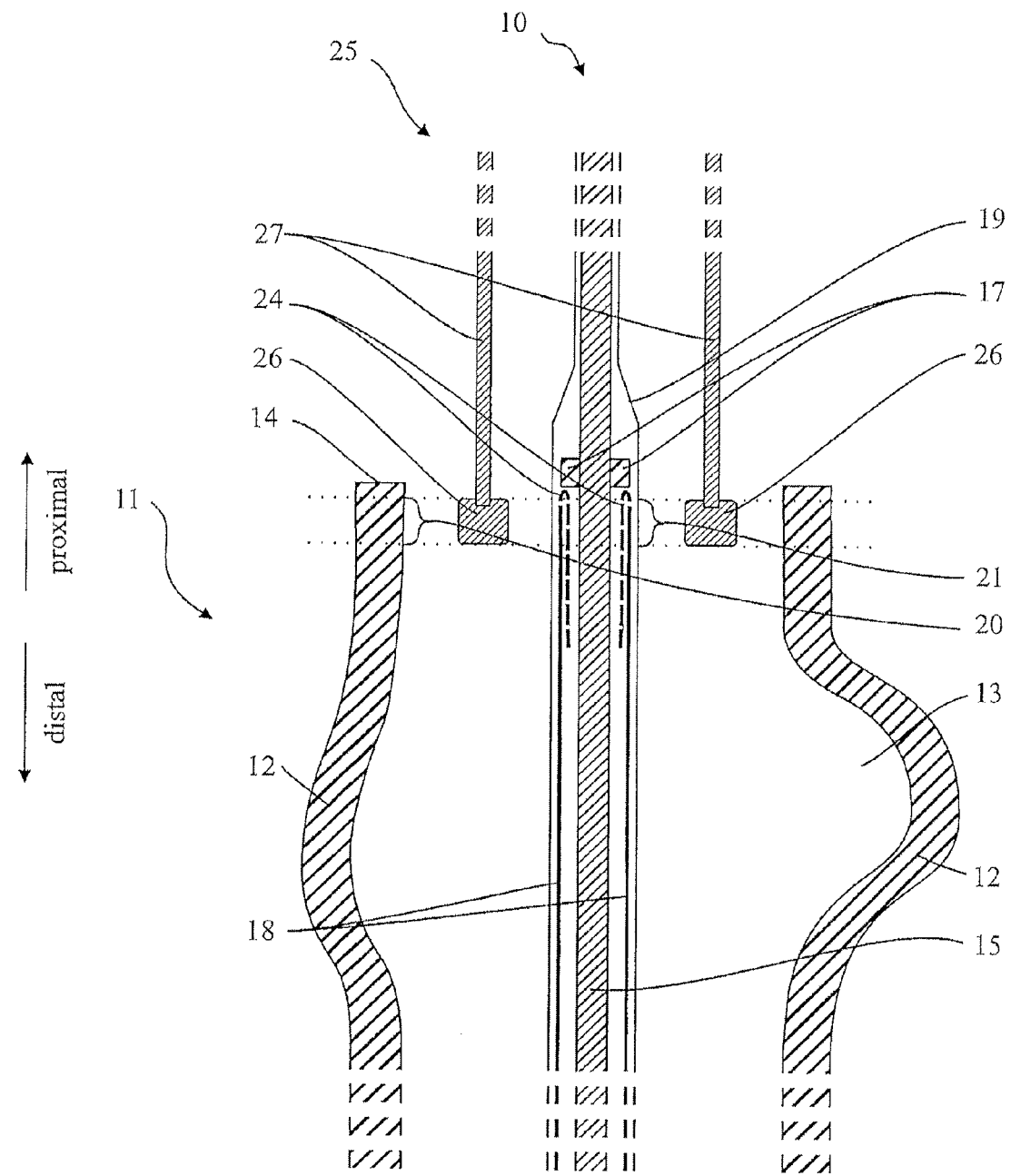

FIG. 8c shows a detail of a sectional view of insertion system 10 of FIG. 8a in the axial direction along the section plane II from FIG. 8b. Here, it is shown in particular that reference mark 26 in its axial position marks deployment zone 21. Further, it is shown that the coincidence of the axial position between deployment zone 21 and landing zone 20 is marked by the position of reference mark 26.

Figure 8D:
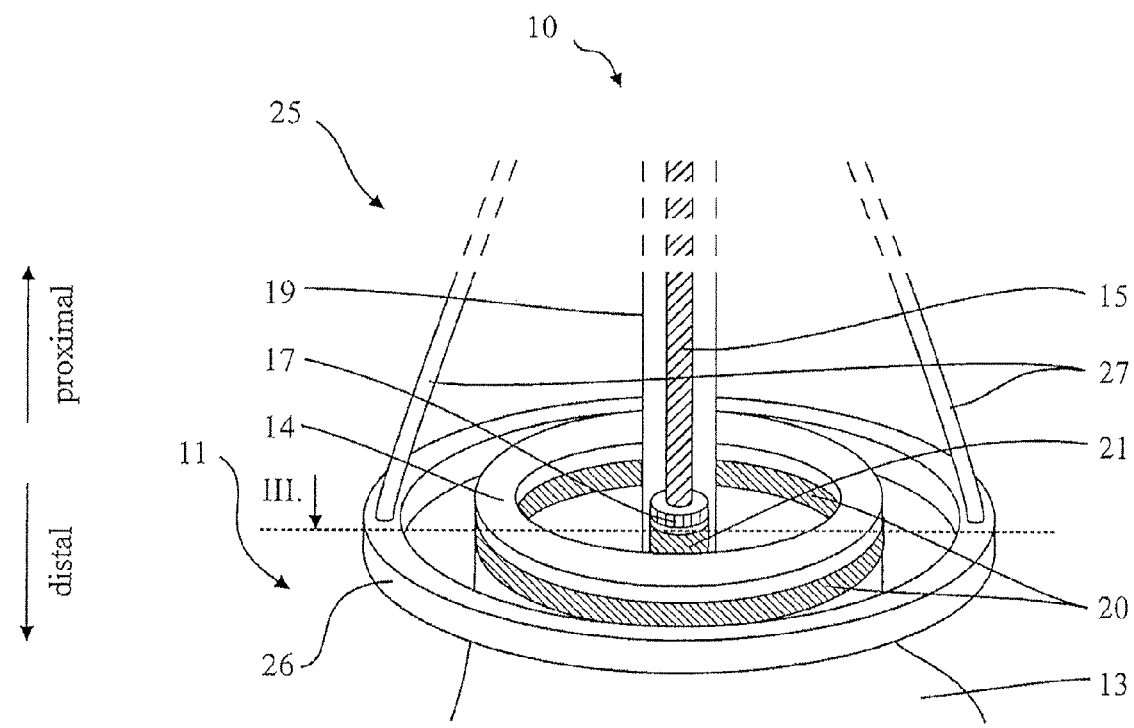

FIG. 8d shows another embodiment of insertion system 10 with reference means 25, in which the reference mark 26 comprises an internal dimension greater than the external diameter of body vessel 11 to be treated. Here, reference mark 26 surrounds body vessel 11 at the same axial level as deployment zone 21 and landing zone 20.

Figure 8E:
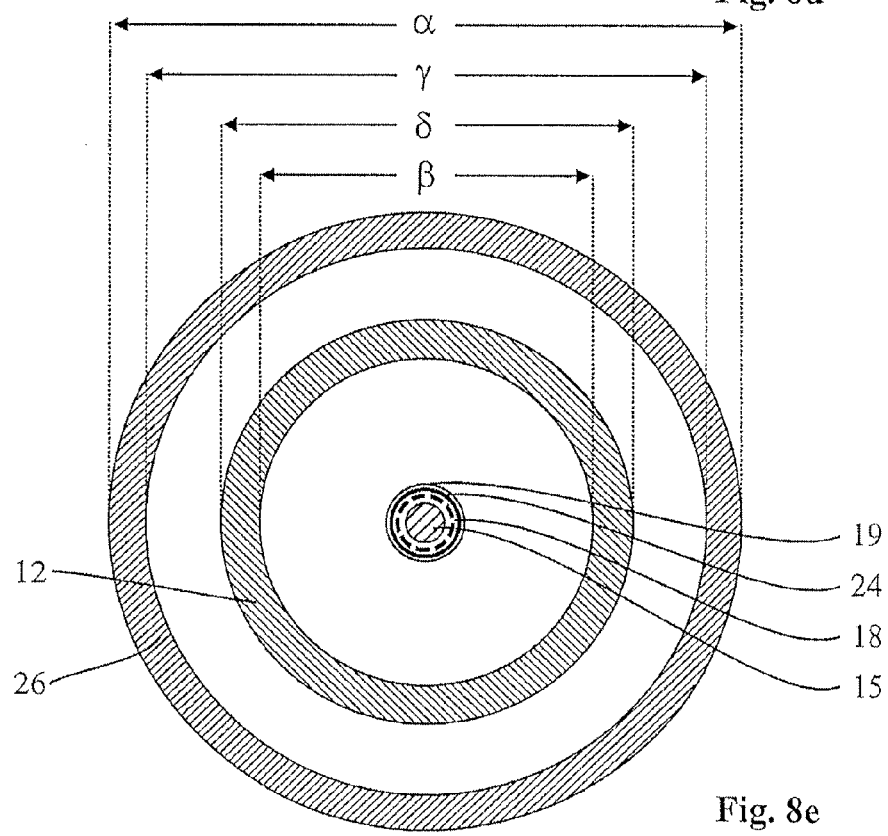

FIG. 8e shows a sectional view of insertion system 10 of FIG. 8d, at the level of the section line III from FIG. 8c. Here, reference mark 26, having internal dimension $\gamma$ and external dimension $\alpha$, is arranged outside of wall 12 of body vessel 11, having internal diameter $\beta$ and external diameter $\delta$. The internal dimension $\gamma$ of reference mark 26, here, is greater than the external diameter $\delta$ of vessel wall 12.

Figure 8F:
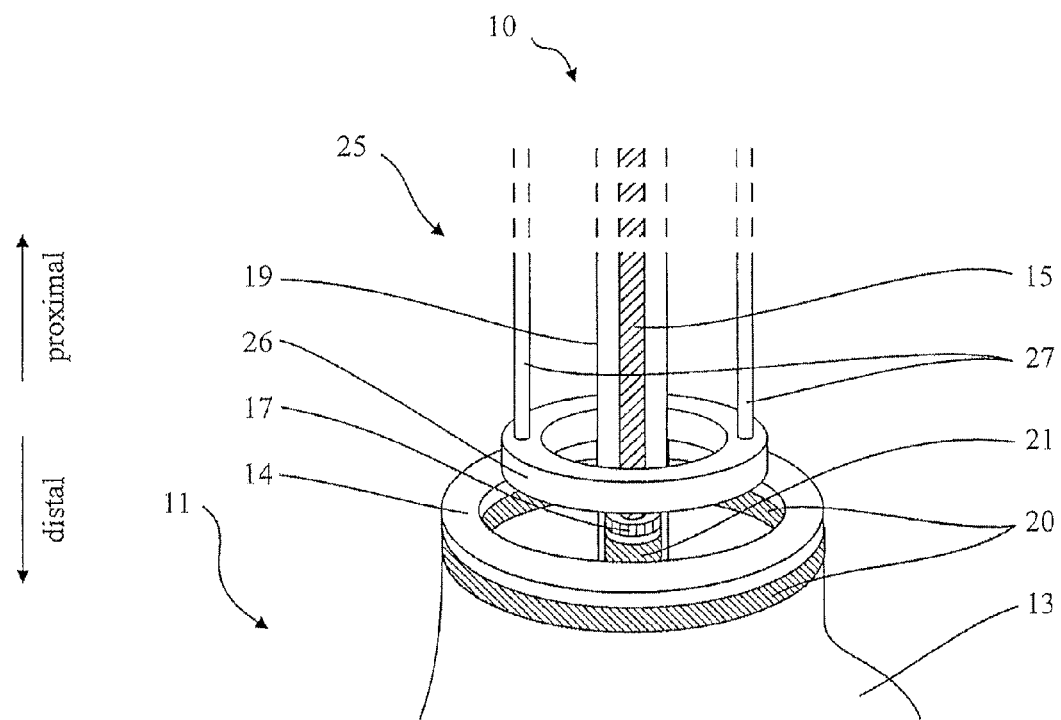

FIG. 8f shows a third embodiment of the novel insertion system 10 with reference mark 26 and holding means 27, which as a whole are designed in such a way that reference mark 26 is located in axial direction proximal to upper margin 14 of body vessel 11, whereas deployment zone 21 is at the same level as landing zone 20.

Figure 9A:
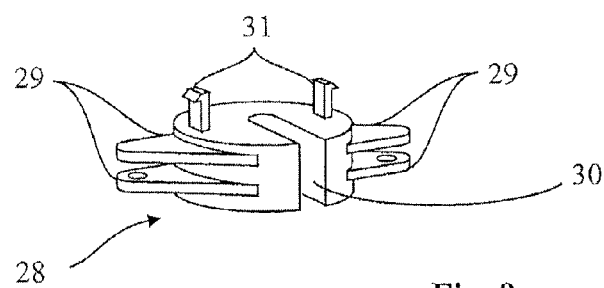
FIGS. 9a to 9g show various embodiments of a holding means head part of the reference means according to the invention.

FIG. 9a shows a first embodiment of holding means head part 28 of the reference means 25 according to the invention, where holding means head part 28 comprises brackets 29 for receiving holding means 27 and acting as spacers between holding means 27 and the second grip 36, recess 30 for releasing the holding means head part 28 from shaft 15, and locking means 31 for securing reference means 25 to first grip 33 in a removable manner.

Figure 9B:
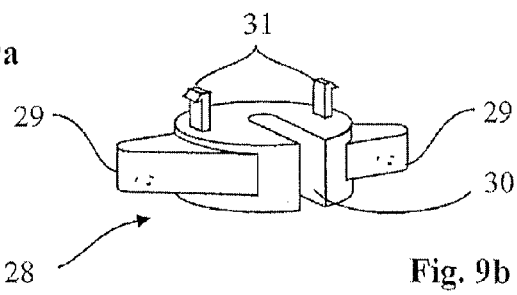

FIG. 9b shows a second embodiment of holding means head part 28 of reference means 25 according to the invention, with brackets 29, recess 30 and locking means 31, wherein each of the brackets 29 is formed in one piece.

Figure 9C:
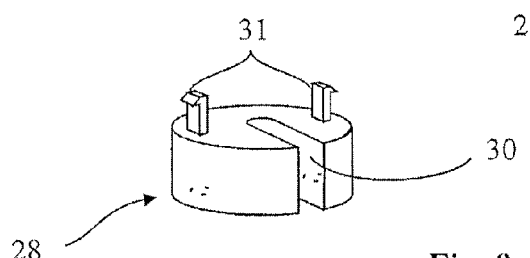

FIG. 9c shows a third embodiment of holding means head part 28, which has recess 30 and locking means 31 but has no brackets, such that holding means 27 are received in the interior of holding means head part 28. This reduces the distance between holding means 27 and shaft 15 as compared to the embodiment with brackets (see FIG. 9a for example).

Figure 9D:
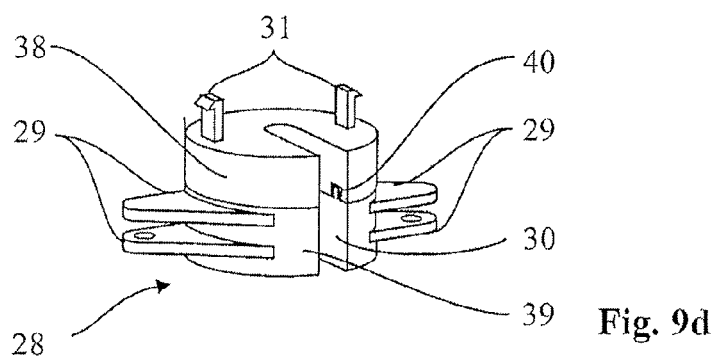

FIG. 9d shows a fourth embodiment of holding means head part 28, wherein holding means head part 28 is divided into a head part top segment 38 and a head part bottom segment 39, wherein head part bottom segment 39 comprises brackets 29, and head part top segment 38 comprises locking means 31.

Moreover, head part top segment 38 and head part bottom segment 39 both comprise recesses 30. Head part top segment 38 is connected to head part bottom segment 39 via a radially encircling holding means 40. Thus, holding means head part 28 can be locked on shaft 15 by turning head part bottom segment 39 relative to head part top segment 38, since recesses 30 then point in different directions.

Figure 9E:
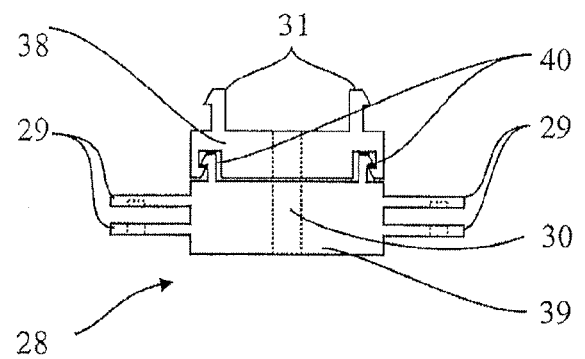

FIG. 9e shows a cross section through the fourth embodiment, as shown in FIG. 9d, of holding means head part 28, with head part top segment 38, head part bottom segment 39, brackets 29, locking means 31, radially encircling holding means 40, and recess 30.

Figure 9F:
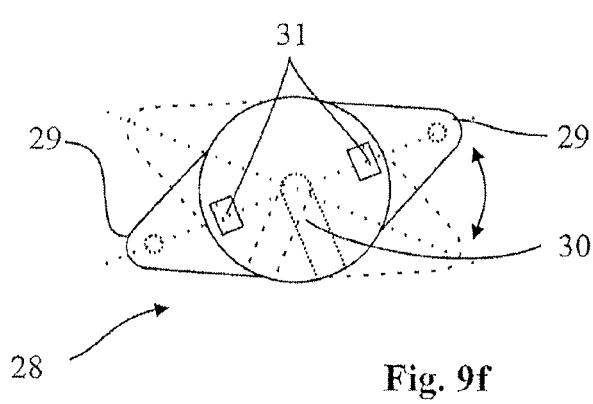

FIG. 9f shows a plan view of the fourth embodiment, as shown in FIG. 9d, of holding means head part 28, showing that brackets 29 are arranged rotatable relative to locking means 31.

Figure 9G:
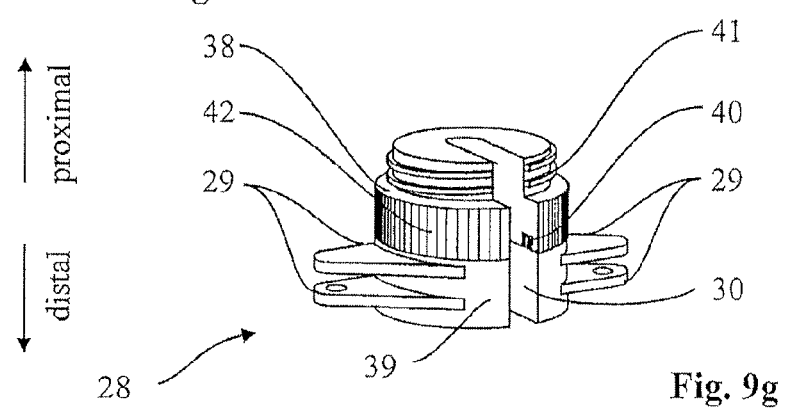

FIG. 9g shows a fifth embodiment of holding means head part 28, in which head part top segment 38 comprises a thread 41 at its proximal portion and comprises a radially encircling knurled surface 42 at its distal portion, and in which head part bottom segment 39 comprises brackets 29, wherein both head part top segment 38 and head part bottom segment 39 comprise a recess 30, and head part top segment 38 is connected to head part bottom segment 39 via said radially encircling holding means 40. The rotatability between head part top segment 38 and head part bottom segment 39 can in this case serve to screw reference means 25 onto a suitable complementary thread on or in the first grip by rotating head part top segment 38, while the rest of the reference means 25, including head part bottom segment 39, holding means 27 and reference mark 26, does not have to be entrained in the direction of rotation.

Therefore, what is claimed is:

1. An insertion system comprising: a self-expanding stent device configured to be released in a body vessel,
    a shaft having an axial direction, said stent device being arranged on said shaft in a first axial position,
    a first grip, which is fixedly connected to said shaft,
    a second grip, which is mounted on said shaft such as to be movable in said axial direction relative to said shaft,
    a sheath, arranged on said shaft and fixedly connected to said second grip for movement relative to said shaft, said sheath having a distal portion, said stent device being arranged inside said distal portion and being radially compressed by said distal portion,
    a reference element configured to continuously monitor an axial position of the stent device relative to said body vessel, and
    rod-shaped holders connected to said reference element and to a holding head that is connected to said shaft.

2. The insertion system of claim 1, wherein the holding head comprises a recess.

3. The insertion system of claim 1, wherein the reference element comprises a recess.

4. The insertion system of claim 1, wherein the holding head is designed as a multi-piece part comprising a head part top segment and at least one head part bottom segment, wherein the head part top segment is movable relative to the head part bottom segment, said head part bottom segment bearing distally on said head part top segment, and wherein the head part top segment comprises means for securing the holding head on said shaft.

5. The insertion system of claim 1, wherein the reference element is shaped substantially annular.

6. The insertion system of claim 1, wherein the reference element comprises an internal dimension greater than an external diameter of a vessel wall of said body vessel to be treated.

7. The insertion system of claim 1, wherein the reference element is arranged axially at substantially the same level as a deployment zone which represents that axial area of the insertion system, on the level whereof the area of the stent device that is to be brought into contact with a landing zone is located after expansion.

8. The insertion system of claim 1, wherein the reference element is axially offset relative to a deployment zone which represents that axial area of the insertion system, on the level whereof the area of the stent device that is to be brought into contact with a landing zone is located after expansion.

9. The insertion system of claim 1, wherein a retention element is provided that is fixedly connected to said shaft and arranged within said sheath, said retention element holding said stent device in its first axial position relative to said first grip.

10. An insertion system comprising: a self-expanding stent device configured to be released in a body vessel,
    a shaft having an axial direction, said stent device being arranged on said shaft in a first axial position,
    a first grip, which is fixedly connected to said shaft,
    a second grip, which is mounted on said shaft such as to be movable in said axial direction relative to said shaft,
    a sheath, arranged on said shaft and fixedly connected to said second grip for movement relative to said shaft, said sheath having a distal portion, said stent device being arranged inside said distal portion and being radially compressed by said distal portion,
    a reference element configured to continuously monitor an axial position of the stent device relative to said body vessel, and
    a holder connected to said reference element and to a holding head that is connected to said shaft, wherein the holding head is designed as a multi-piece part comprising a head part top segment and at least one head part bottom segment, wherein the head part top segment is movable relative to the head part bottom segment, said head part bottom segment bearing distally on said head part top segment, and wherein the head part top segment comprises means for securing the holding head on said shaft.

11. The insertion system of claim 10, wherein the holding head comprises a recess.

12. The insertion system of claim 10, wherein the reference element comprises a recess.

13. The insertion system of claim 10, wherein the reference element is shaped substantially annular.

* * * * *